US009216029B1

(12) United States Patent
Hahn et al.

(10) Patent No.: US 9,216,029 B1
(45) Date of Patent: Dec. 22, 2015

(54) SURGICAL FORCEPS

(71) Applicant: Alfred E. Mann Institute for Biomedical Engineering at the University of Southern California, Los Angeles, CA (US)

(72) Inventors: Ricardo G. Hahn, Ojai, CA (US); Afshin Nadershahi, Northridge, CA (US); Sudeep Deshpande, Newbury Park, CA (US)

(73) Assignee: ALFRED E. MANN INSTITUTE FOR BIOMEDICAL ENGINEERING AT THE UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 14/835,509

(22) Filed: Aug. 25, 2015

Related U.S. Application Data

(62) Division of application No. 13/689,499, filed on Nov. 29, 2012, now abandoned.

(60) Provisional application No. 61/565,628, filed on Dec. 1, 2011.

(51) Int. Cl.
*A61B 17/00* (2006.01)
*A61B 17/28* (2006.01)
*A61F 6/20* (2006.01)

(52) U.S. Cl.
CPC ............... *A61B 17/282* (2013.01); *A61F 6/202* (2013.01); *A61F 6/206* (2013.01)

(58) Field of Classification Search
CPC . A61B 17/28; A61B 17/30; A61B 2017/2902
USPC .............................. 606/205–211, 99; 294/99.2
See application file for complete search history.

(56) References Cited

U.S. PATENT DOCUMENTS

| 4,803,983 | A | 2/1989 | Siegel |
| 5,011,491 | A | 4/1991 | Boenko et al. |

(Continued)

FOREIGN PATENT DOCUMENTS

WO    2011/038299 A2    3/2011

OTHER PUBLICATIONS

International Search Report and Written Opinion of the International Searching Authority, dated Feb. 6, 2013, for PCT Application PCT/US2012/067441, filed Nov. 30, 2012, entitled "Surgical Forceps."

*Primary Examiner* — Todd E Manahan
*Assistant Examiner* — Majid Jamialahmadi
(74) *Attorney, Agent, or Firm* — McDermott Will & Emery LLP

(57) ABSTRACT

This application presents a bifurcated, optimally-angled surgical forceps. In one example, this surgical forceps may enable a more natural maneuver for initial clamping of the vas deferens through the scrotal skin. This may be more comfortable for users and easier to maintain, and may provide greater tactile surface contact between the thumb and vas deferens. This device also may provide the surgeon with an entire segment of vas deferens upon which the vasectomy may be performed, thus reducing the need for frequent repositioning of instruments. The device may also be applied to other surgical procedures that may benefit from the features of the device and where a section of a tubular anatomical structure may need clamping at two points along its length. Examples include blood and lymphatic vessels, ducts of the digestive system, and large nerves or nerve bundles.

2 Claims, 3 Drawing Sheets

(56) References Cited

U.S. PATENT DOCUMENTS

| | | |
|---|---|---|
| 2002/0183770 A1 | 12/2002 | Anderson |
| 2005/0033353 A1* | 2/2005 | Jones .................. A61B 17/282 |
| | | 606/205 |
| 2007/0219582 A1 | 9/2007 | Brunelle et al. |
| 2011/0208236 A1* | 8/2011 | Ward ..................... A61B 10/06 |
| | | 606/205 |
| 2012/0059407 A1 | 3/2012 | Isch et al. |

* cited by examiner

SURGICAL FORCEPS

CROSS-REFERENCE TO RELATED APPLICATIONS

This application is a divisional application of U.S. patent application Ser. No. 13/689,499, filed Nov. 29, 2012, entitled "Surgical Forceps"; which is based upon and claims priority to U.S. Provisional Application Ser. No. 61/565,628, filed Dec. 1, 2011, entitled "Vasectomy Forceps," the entire content of which is incorporated herein by reference.

BACKGROUND

1. Field

This application relates generally to medical instruments, particularly surgical forceps for examinations and operations. This application further relates to vasectomy forceps. This application also relates to performing a vasectomy.

2. General Background and State of the Art

Vasectomy is a male birth control surgical procedure that involves severing the vas deferens and tying and/or sealing the ends, preventing the entry of sperm into the seminal stream. The procedure is often carried out in a physician's office or clinic and is done under local anesthesia. The two widely used methods for performing a vasectomy are "traditional" and "no-scalpel."

In the "traditional" method, the surgeon makes an incision on the scrotum to access and directly clamp the vas deferens. The surgeon then occludes a small piece of the vas deferens and seals the ends by suturing, cauterizing or applying surgical clips, or employing a combination of sealing methods. The procedure is done for both vas deferentia.

The "no-scalpel" method involves the surgeon accessing the vas deferens by puncturing the scrotum with a sharp hemostat, usually after clamping the vas deferens through the scrotal skin. The surgeon first locates the vas deferens through the scrotum, typically by rolling the vas deferens between the thumb, index and middle fingers. Efficiency in locating the vas deferens by feel requires experience. Once the vas deferens has been located and isolated from other structures through the scrotal skin, it is pushed toward the surface to enable clamping. In general practice, the surgeon uses one finger on the underside of the pinched scrotal skin to push the vas deferens between his two fingers on the opposing (upper) side. This forces a segment of the vas deferens to a position close to the surface where it can be clamped.

The vas deferens is exposed from the puncture site using various forceps. The surgeon then occludes the vas deferens and seals the severed ends by suturing, cauterizing or applying surgical clips, or employing a combination of sealing methods. The procedure is done for both vas deferentia. No-scalpel vasectomy was disclosed in detail in a document entitled "No-Scalpel Vasectomy. A Training Course for Vasectomy Providers and Assistants" $2^{nd}$ Edition, published by EngenderHealth in 2007. Entire content of this document is incorporated herein by reference.

Various types of vasectomy forceps used to clamp the vas deferens are available in the market. Most forceps used in vasectomies consist of an intersecting pair of scissoring arms with a ratcheting mechanism to maintain the desired clamping pressure and tips shaped to grasp the tissue (in this case the vas deferens) in a certain way. For example, the distal end of the ring-type vasectomy forceps consists of a single pair of half-hooks on opposing arms that come together to form a ring, between which the vas deferens is clamped. Often, several types of forceps are used in a single procedure. A plurality of forceps may be used simultaneously to clamp the exposed vas deferens at two locations, enabling the surgeon to occlude and seal the vas deferens between two clamped points.

The following are a few types of commonly used vasectomy forceps available in the market: ring-type (cantilevered or non-cantilevered); teardrop; ball-end (non-penetrating); hemostat (Mosquito forceps—Halstrad or Kelly; curved or straight); and tissue forceps (Allis forceps or surgical tweezers).

Several problems with current tools and methods of no-scalpel vasectomy exist. For example, the wrist action currently required to push the vas deferens to the surface of the scrotum feels unnatural, is uncomfortable, and is difficult to maintain. Furthermore, the use of the index finger, middle finger, or tip of the thumb to push the vas deferens between the other two fingers provides little tactile surface against the vas deferens, making isolation and positioning of the vas deferens difficult.

Additionally, existing forceps require much maneuvering and transferring of the vas deferens between different forceps throughout the procedure, in order to occlude and seal the vas deferens on both sides of the clamp.

Furthermore, during surgery, the surgeon typically locates the vas deferens from the exterior of the scrotum by rolling the vas deferens between the fingers and thumb. Once the vas deferens is located and the segment is pushed outward towards the surgeon, the approach direction for clamping the vas deferens is often from the side (along the patient's abdomen) rather than from the top of the patient. The grasping and clamping of the vas deferens with a straight tool in this position typically make it cumbersome for the surgeon. Use of a straight tool would further occlude the intended clamping site.

SUMMARY

This application presents surgical forceps that may be used to clamp tubular anatomical structures at least at two points.

For example, this surgical forceps enables a more natural maneuver for initial clamping of the vas deferens through the scrotal skin, as it is clamped on both sides of a downwardly pressed thumb (against pressure from the index and middle fingers on the opposing side of the pinched scrotal skin). This maneuver resembles that commonly used in routine physical examinations, which is more familiar to practitioners, is more comfortable and easier to maintain given its more natural wrist position, and provides greater tactile surface contact between the thumb and vas deferens. This device may therefore be especially beneficial for less experienced surgeons who perform vasectomies. The device may additionally provide a hemostatic function by compressing small blood vessels at each end of a segment of vas deferens, thereby keeping the surgical site clear of blood.

This surgical forceps also provides the surgeon with an entire segment of vas deferens (not just a clamped loop) upon which the vasectomy may be performed, thus reducing the need for frequent repositioning of instruments. Once the vas deferens is located, grasped and clamped, local anesthetic may then easily be injected at each end of the vas deferens segment. The vasectomy forceps reduces the need to constantly re-adjust the surgical site while providing a means to manipulate the surgical site without losing grasp over the segment of vas deferens.

The surgical forceps may also be applied to other surgical procedures that may benefit from the features of the device and where a section of a tube-type vessel or duct may need clamping at two points along its length. Examples include blood and lymphatic vessels, ducts of the digestive system, and large nerves or nerve bundles.

The surgical forceps has a proximal end and a distal end. The surgical forceps may comprise a first elongated arm, a second elongated arm, a hinge, a first finger grip at the proximal end of the first elongated arm, a second finger grip at the proximal end of the second elongated arm, a ratcheting mechanism, a first jaw at a distal end of the first elongated arm, and a second jaw at a distal end of the second elongated arm. The first elongated arm and the second elongated arm may be pivoted at the hinge.

The ratcheting mechanism may comprise a first ratchet on the first elongated arm adjacent to the first finger grip and a second ratchet on the second elongated arm adjacent to the second finger grip. The first ratchet may engage with the second ratchet as the finger grips are brought toward one another.

The first jaw may be bifurcated to form a first branch and a second branch. The first branch may further comprise a first tip at the distal end of the surgical forceps. The second branch may further comprise a second tip at the distal end of the surgical forceps.

The second jaw may be bifurcated to form a third branch and a fourth branch. The third branch may further comprise a third tip at the distal end of the surgical forceps. The fourth branch may further comprise a fourth tip at the distal end of the surgical forceps. The first curved enclosure and the second curved enclosure may be both circular. The first curved enclosure and the second curved enclosure may have the same diameter. The same diameter may be at least 3 millimeters. The same diameter may vary in the range of 3 millimeters to 5 millimeters.

When the ratchets are engaged, the first tip and the third tip may form a first curved enclosure, and the second tip and the fourth tip may form a second curved enclosure.

When the ratchets are engaged; the first jaw and the second jaw may form a first plane. The first finger grip, the second finger grip, the first elongated arm, and the second elongated arm may form a second plane. In one embodiment, the first plane and the second plane may be perpendicular to each other. In another embodiment, the first plane and the second plane may be at an oblique angle to each other.

The first elongated arm, the second elongated arm, the hinge, or combinations thereof may be bent at an angle. In one embodiment, the first elongated arm and the second elongated arm may be both bent at an angle. In another embodiment, the hinge may be bent at an angle.

The surgical forceps may further comprise a stem located between the hinge and the distal end of the surgical forceps. The stem may have a broad base.

The distance between the two branches of the first jaw and the distance between the two branches of the second jaw may be equal. This equal distance may be at least 10 millimeters. This equal distance may also vary within the range of 10 millimeters to 30 millimeters.

The tips may be configured to apply at least one surgical clip.

This application further presents a method that may use surgical forceps to perform a vasectomy. This method may comprise pinching the vas deferens with fingers, clamping the vas deferens with the surgical forceps at two locations, and occluding the vas deferens. In another embodiment, this method may comprise pinching the vas deferens with fingers, clamping the vas deferens with the surgical forceps at two locations, separating the vas deferens from the surrounding tissue, and flipping the surgical forceps prior to occluding the vas deferens.

It is understood that other embodiments of the devices and methods will become readily apparent to those skilled in the art from the following detailed description, wherein only exemplary embodiments of the devices, methods and systems are shown and described by way of illustration. As will be realized, the devices and systems are capable of other and different embodiments and their several details are capable of modification in various other respects, all without departing from the spirit and scope of the invention. Accordingly, the drawings and detailed description are to be regarded as illustrative in nature and not as restrictive.

BRIEF DESCRIPTION OF THE DRAWINGS

Aspects of the surgical forceps are illustrated by way of example, and not by way of limitation, in the accompanying drawings, wherein.

DETAILED DESCRIPTION

The detailed description set forth below in connection with the appended drawings is intended as a description of exemplary embodiments and is not intended to represent the only embodiments in which the retractors can be practiced. The term "exemplary" used throughout this description means "serving as an example, instance, or illustration," and should not necessarily be construed as preferred or advantageous over other embodiments. The detailed description includes specific details for the purpose of providing a thorough understanding of the retractors. However, it will be apparent to those skilled in the art that the forceps and may be practiced without these specific details.

This application presents surgical forceps that may be used to clamp tubular anatomical structures at least at two points.

Figure 1:
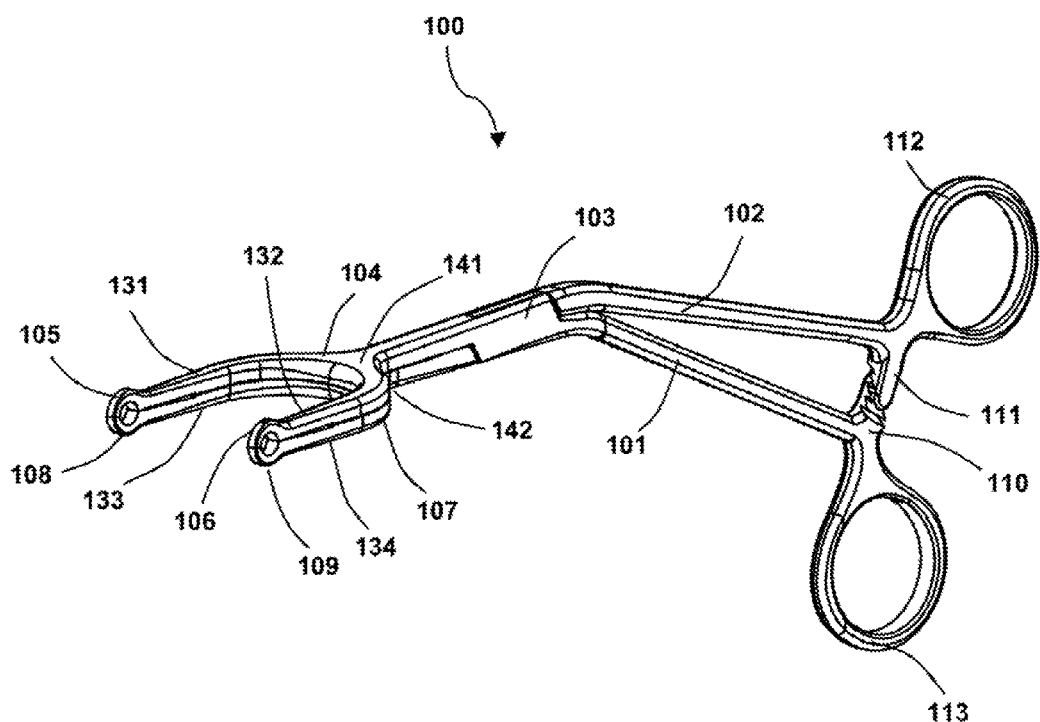
FIG. 1 is an isometric view of an exemplary surgical forceps in a closed position.
Figure 2:
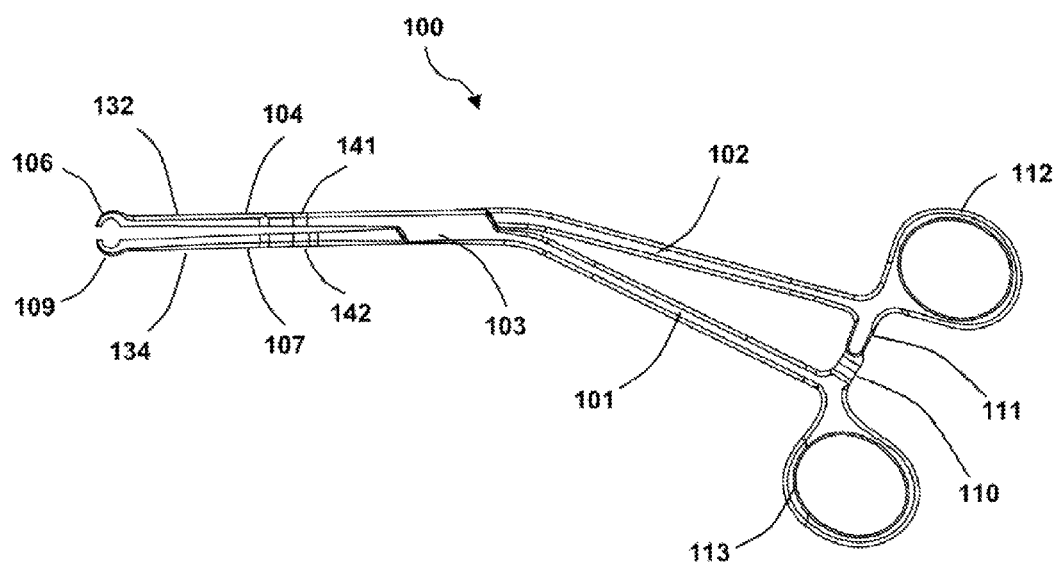
FIG. 2 is a side view of the exemplary surgical forceps of FIG. 1 in a slightly open position.
Figure 3:
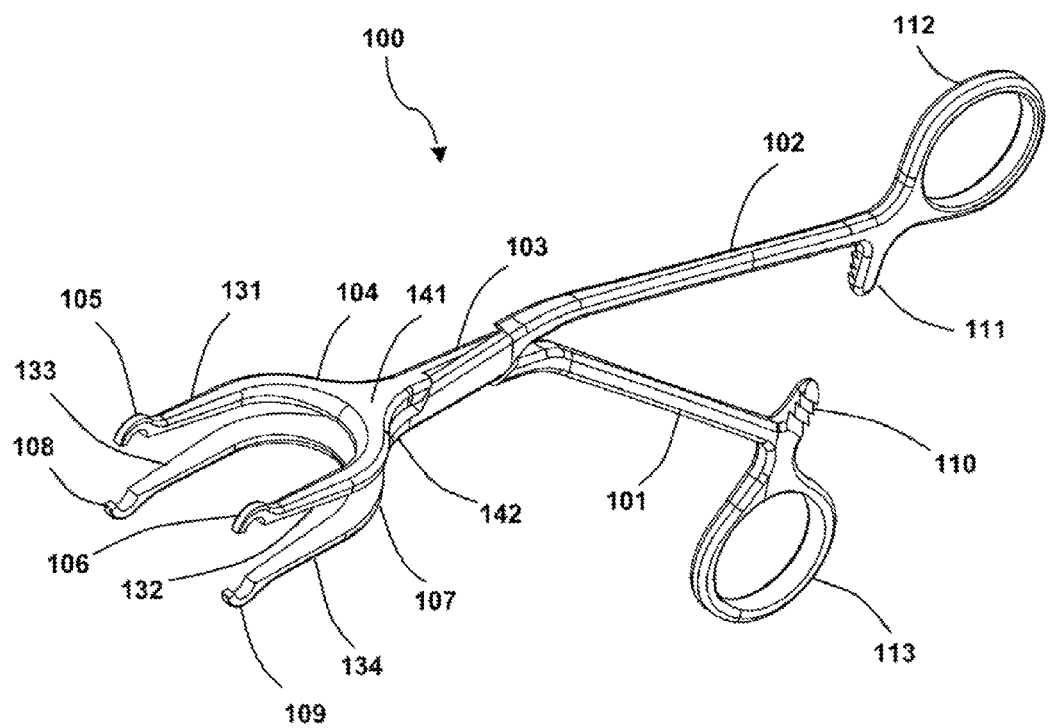
FIG. 3 is an isometric view of the exemplary surgical forceps of FIG. 1 in an open position.

FIG. 1 depicts an isometric view of an exemplary surgical forceps 100 in a closed position, and FIG. 2 depicts a side view of the exemplary surgical forceps 100 of FIG. 1 in a slightly open position. FIG. 3 depicts a side view of the exemplary surgical forceps 100 of FIG. 1 in an open position. The surgical forceps may be constructed with a rigid material such as metal or plastic. The forceps may be re-usable or single-use disposable.

A surgical forceps has a proximal end and a distal end and may comprise a first elongated arm 101 and a second elongated arm 102, a hinge 103, a first finger grip 113 at the proximal end of the first elongated arm, a second finger grip 112 at the proximal end of the second elongated arm, a ratcheting mechanism comprising a first ratchet 110 on the first arm adjacent to the first finger grip and a second ratchet 111 on the second arm adjacent to the second finger grip, a first jaw 104 at a distal end of the first elongated arm, and a second jaw 107 at a distal end of the second elongated arm. The first elongated arm 101 and the second elongated arm 102 may be pivoted at the hinge 103. The first ratchet 110 may engage with the second ratchet 111 as the finger grips are brought toward one another. The first jaw may be bifurcated to form a first branch 131 and a second branch 132. The first branch 131 may further comprise a first tip 105 at the distal end of the surgical forceps. The second branch 132 may further comprise a second tip 106. The second jaw 107 may be bifurcated to form a third branch 133 and a fourth branch 134. The third branch 133 may further comprise a third tip 108 at the distal end of the surgical forceps. The fourth branch 134 may further comprise a fourth tip 109.

Each elongated arm 101 and 102 may be pivoted at the hinge 103 to create the scissoring action. Finger grips 113 and 112 may allow a user to place her fingers in and operate the forceps at one end while engaging the jaws 104 and 107 for the clamping action at the other. The user may use the ratcheting mechanism to lock the forceps in the desired position. The finger grips 113 and 112 side of the forceps shall be referred to as the proximal end while the jaw 104 and 107 side of the forceps shall be referred to as the distal end.

When the ratchets 110 and 111 are engaged; the first jaw 104 and the second jaw 107 may form a first plane; and the first finger grip 113 together with the first elongated arm 101 and the second finger grip 112 together with the second elongated arm 102 may form a second plane. The first plane and the second plane may be at a perpendicular or an oblique angle to each other.

The surgical forceps may further comprise stems 141 and 142 located between the hinge and the distal end of the surgical forceps. The stems 141 and 142 may have a broad base to provide strength and stability against bending and misalignment of the jaws when the elongated arms are brought together repetitively after many surgical procedures.

In one embodiment, the tips 105, 106, 108 and 109 may be flat. In another embodiment, the tips may individually be curved. The tip may have any curved shape. Examples of the curved shapes are circular, elliptical, oval, undulated, and teardrop shapes. Square, rectangular and triangular tips are also possible. Combinations of these shapes are also possible.

In one embodiment, the first branch 131 may further comprise a first tip 105 at the distal end of the surgical forceps 100. The second branch 132 may further comprise a second tip 106. The third branch 133 may further comprise a third tip 108 at the distal end of the surgical forceps 100. The fourth branch 134 may further comprise a fourth tip 109. In one embodiment, when the ratchets are engaged, the first tip opposes the third tip, and the second tip opposes the fourth tip. The first tip and the third tip may form a first enclosure, and the second tip and the fourth tip may form a second enclosure. The first enclosure and the second enclosure may be curved. The first enclosure and the second enclosure may also be circular. The first circular enclosure and the second circular enclosure may have the same diameter. The diameter of these enclosures may be at least 3 millimeters for surgical operations involving the vas deferens. The at least 3 millimeters diameters may also be suitable for surgical operations involving variety of tubular anatomic structures, for example, some larger diameter blood vessels, intestines, fallopian tubes, and bile duct. The diameter of these circular enclosures may vary in the range of 3 millimeters to 5 millimeters. The circular enclosure diameters smaller than 3 millimeters are also possible, for example, for surgical operations involving nerves, smaller diameter blood vessels, and nerve sheaths.

In an exemplary embodiment, at the distal end, the tips 105, 106, 108 and 109 may come together when the user brings the elongated arms 101 and 102 to a closed position. In another embodiment, the tips 105, 106, 108 and 109 may form an enclosure in the closed position of the device as shown in FIG. 1. In yet another embodiment, the enclosures formed by the tips 105, 106, 108 and 109 may clamp the vas deferens through the scrotal skin. The enclosures formed by the tips 105, 106, 108 and 109 may also provide a hemostatic function by compressing small blood vessels at each end of a segment of vas deferens, thereby keeping the surgical site clear of blood. The diameter of the circular enclosures may be in the range of 3 millimeters to 5 millimeters to accommodate the vas deferens and thickness of the scrotal skin. In an exemplary embodiment, the circular enclosure diameter may be about 4 millimeters. This about 4 millimeters circular enclosure diameter may provide a deeper grasping action to clamp around the vas deferens through the scrotum.

During the vasectomy, the thumb and located vas deferens segment may be passed between the branches of each jaw and the vas deferens segment may then be grasped by the tips and clamped in place. In one embodiment, the distance between the two branches of the first jaw 104 and the distance between the two branches of the second jaw 107 may have equal distance. This equal distance may be at least 10 millimeters to accommodate the width of a human thumb tip for surgical operations involving the vas deferens. The equal distance may vary in the range of 10 millimeters to 30 millimeters to surgically operate on the vas deferens. For other types of surgical operations, the equal distance may suitable vary to accommodate different lengths of anatomical structures.

In the exemplary embodiment of FIGS. 1-3, the surgical forceps 100 may be angled to improve visibility and access to the scrotum and vas deferens. The angled forceps may provide the surgeon with improved visualization and reduced time for grasping, while the ergonomic design of the forceps provides for comfortable application of the device onto the scrotum. In one embodiment, the forceps may be flipped after clamping the vas deferens to angle the tips upward to hoist the vas deferens up from the surgical field, thereby providing the surgeon with a better presentation of the surgical site.

The surgical forceps may be bent at the first elongated arm 101, the second elongated arm 102, the hinge 103, or combinations thereof. For example, the surgical forceps may be bent at both the first elongated arm and the second elongated arm to provide the angled forceps. In another example, the hinge may be bent to provide the angled forceps. In yet another example, the first elongated arm, the second elongated arm, and the hinge are all bent to provide the angled forceps.

In an exemplary embodiment, the bending angle of the angled forceps may vary in the range of 120 degrees to 160 degrees. In an exemplary embodiment, the bending angle may be at about 155 degrees.

Once clamped, the device may remain in the clamped state until the vas deferens is exposed and/or occluded. The locking mechanism may be released on completion of the surgical procedure.

Once the vas is brought into the open, it may be occluded using a variety of methods. Examples of these methods are cutting, ligation with sutures, division, cautery, application of clips, excision of a segment of the vas, fascial interposition, and combination thereof. Ligation may be preferred. For example, ligation with excision and fascial interposition may be preferred.

In one embodiment, the tips 105, 106, 108 and 109 may serve as seats for surgical clips used for closing the occluded ends of a tubular anatomical structure, for example the vas deferens, similar to a crimping tool.

In an alternate exemplary embodiment (not shown), the tips may be separated by a gap while the forceps are in substantially fully closed position. This gap may prevent the tips from puncturing the scrotum and scarring the skin. In the exemplary embodiment, the gap between the opposed tips may range from 0.5 millimeter to 2 millimeters to accommodate the scrotum skin thickness while effectively clamping the vas deferens.

This application further presents a method that uses surgical forceps to perform a vasectomy. In an exemplary method, performing the vasectomy may comprise pinching the vas deferens with fingers, clamping the vas deferens at two different points using any embodiment of the surgical forceps disclosed above, and occluding the vas deferens. This exemplary method may further comprise flipping the surgical forceps prior to occluding the vas deferens. The angled forceps may be more suitable for the flipping action.

The previous description of the disclosed embodiments is provided to enable any person skilled in the art to make or use the surgical forceps. Various modifications to these embodiments will be readily apparent to those skilled in the art, and the generic principles defined herein may be applied to other embodiments without departing from the spirit or scope of the surgical forceps. Thus, the surgical forceps and methods of performing vasectomy are not intended to be limited to the embodiments shown herein but are to be accorded the widest scope consistent with the principles and novel features disclosed herein.

We claim:

1. A method for performing a vasectomy comprising:
pinching a vas deferens with fingers;
clamping the vas deferens at two locations with a surgical forceps comprising:
  a first elongated arm and a second elongated arm;
  a hinge, wherein the first elongated arm and the second elongated arm are pivoted at the hinge;
  a first finger grip at the proximal end of the first elongated arm;
  a second finger grip at the proximal end of the second elongated arm;
  a ratcheting mechanism comprising a first ratchet on the first elongated arm adjacent to the first finger grip and a second ratchet on the second elongated arm adjacent to the second finger grip, wherein the first ratchet engages with the second ratchet as the finger grips are brought toward one another;
  a first jaw at a distal end of the first elongated arm, wherein the first jaw is bifurcated to form a first branch and a second branch; and wherein the first branch further comprises a first tip at the distal end of the surgical forceps, and wherein the second branch further comprises a second tip at the distal end of the surgical forceps; and
  a second jaw at a distal end of the second elongated arm, wherein the second jaw is bifurcated to form a third branch and a fourth branch,
  wherein the third branch further comprises a third tip at the distal end of the surgical forceps,
  wherein the fourth branch further comprises a fourth tip at the distal end of the surgical forceps, and
  wherein, when the ratchets are engaged, the first tip and the third tip form a first curved enclosure, and the second tip and the fourth tip form a second curved enclosure; said vas deferens being clamped in said first and second curved enclosures; and
occluding the vas deferens.

2. A method for performing a vasectomy comprising:
pinching a vas deferens with fingers;
clamping the vas deferens at two locations with a surgical forceps comprising:
  a first elongated arm and a second elongated arm;
  a hinge, wherein the first elongated arm and the second elongated arm are pivoted at the hinge;
  a first finger grip at the proximal end of the first elongated arm;
  a second finger grip at the proximal end of the second elongated arm;
  a ratcheting mechanism comprising a first ratchet on the first elongated arm adjacent to the first finger grip and a second ratchet on the second elongated arm adjacent to the second finger grip, wherein the first ratchet engages with the second ratchet as the finger grips are brought toward one another;
  a first jaw at a distal end of the first elongated arm, wherein the first jaw is bifurcated to form a first branch and a second branch; and wherein the first branch further comprises a first tip at the distal end of the surgical forceps, and wherein the second branch further comprises a second tip at the distal end of the surgical forceps; and
  a second jaw at a distal end of the second elongated arm, wherein the second jaw is bifurcated to form a third branch and a fourth branch,
  wherein the third branch further comprises a third tip at the distal end of the surgical forceps,
  wherein the fourth branch further comprises a fourth tip at the distal end of the surgical forceps,
  wherein, when the ratchets are engaged, the first tip and the third tip form a first curved enclosure, and the second tip and the fourth tip form a second curved enclosure, said vas deferens being clamped in said first and second curved enclosures; and
  wherein the first elongated arm, the second elongated arm, the hinge, or combinations thereof are bent at an angle;
separating the vas deferens from the surrounding tissue, and
flipping the surgical forceps prior to occluding the vas deferens.

\* \* \* \* \*